United States Patent [19]

Thomas et al.

[11] Patent Number: 4,665,181

[45] Date of Patent: May 12, 1987

[54] ANTI-INFLAMMATORY PHTHALAZINONES

[75] Inventors: Telfer L. Thomas, Pittsford; Lesley A. Radov, Penfield, both of N.Y.

[73] Assignee: Pennwalt Corporation, Philadelphia, Pa.

[21] Appl. No.: 611,310

[22] Filed: May 17, 1984

[51] Int. Cl.$^4$ ............... C07D 237/32; C07D 401/04; C07D 401/06; A61K 31/50
[52] U.S. Cl. ............................... 544/237; 540/481; 540/599
[58] Field of Search ............ 544/237; 250/243.3; 540/481

[56] References Cited

U.S. PATENT DOCUMENTS 3,845,052 10/1974 Stachel .................. 544/237
4,134,880 1/1979 Eberlein et al. ......... 544/237
4,334,069 6/1982 Buckler ................. 544/237

FOREIGN PATENT DOCUMENTS 2632656 2/1977 Fed. Rep. of Germany .
2433017 3/1980 France .
1126669 9/1968 United Kingdom .
2055825 5/1981 United Kingdom .

OTHER PUBLICATIONS

Amano et al, Chem. Abs. 88, 37431j.

Primary Examiner—Mark L. Berch

[57] ABSTRACT

A compound useful as anti-inflammatory agents in warm-blooded animals of the formula

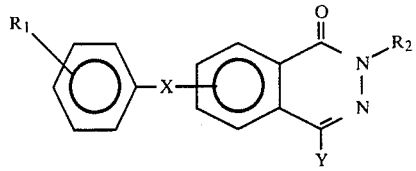

wherein
X is a member of the class of ethylene and ethenyl and is substituted for hydrogen in the sixth or seventh position of the 1(2H)-phthalazinone ring
Y is a member of the class of hydrogen and hydroxyl
$R_1$ is a member of the class of hydrogen, alkyl, alkoxy, hydroxyl, halogen, nitro, $-NR_3R_4$, $-COR_5$ and $-O-A$ wherein A is a mineral acid residue which with $-O-$ forms an ester or the alkali metal salt of said ester,
$R_2$ is a member of the class of hydrogen, alkyl, phenyl, substituted phenyl, heteroaryl, hydroxyalkylene, polyhydroxyalkylene, aminoalkylene, alkylaminoalkylene, and carboxyalkylene,
$R_3$, $R_4$ are independently from the class of hydrogen, alkyl, aminoalkylene or alkylaminoalkylene,
$R_5$ is a member of the class of $OR_3$ and

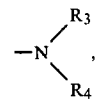

for example hydroxyl, methoxyl, 2-dimethylaminoethoxyl or 2-dimethylaminoethylamino, and wherein by alkyl and alkylene is meant respectively a mono- or divalent saturated aliphatic radical containing up to about eight carbon atoms, wherein the nitrogen of the alkylamino or alkylaminoalkylene may form a heterocycle with the alkyl or alkylene groups, wherein substituted phenyl may be substituted by, for example, alkyl, hydroxyl, alkoxy, halogen, nitro or amino, wherein heteroaryl may be, for example, 2-pyridyl.

23 Claims, No Drawings

ANTI-INFLAMMATORY PHTHALAZINONES

STATEMENT OF THE INVENTION

The present invention provides a phthalazin-1(2H)one of the formula

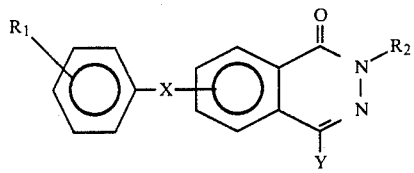

and pharmaceutically acceptable acid or base salts thereof wherein

X is a member of the class of ethylene and ethenyl and is substituted for hydrogen in the sixth or seventh position of the 1(2H)-phthalazinone ring Y is a member of the class of hydrogen and hydroxyl $R_1$ is a member of the class of hydrogen, alkyl, alkoxy, hydroxyl, halogen, nitro, —$NR_3R_4$, —$COR_5$ and —O—A wherein A is a mineral acid residue which with —O— forms an ester or the alkali metal salt of said ester, $R_2$ is a member of the class of hydrogen, alkyl, phenyl, substituted phenyl, heteroaryl, hydroxyalkylene, polyhydroxyalkylene, aminoalkylene, alkylaminoalkylene, and carboxyalkylene, $R_3, R_4$ are independently from the class of hydrogen, alkyl, aminoalkylene or alkylaminoalkylene, $R_5$ is a member of the class of $OR_3$ and

for example hydroxyl, methoxyl, 2-dimethylaminoethoxyl or 2-dimethylaminoethylamino, and wherein by alkyl and alkylene is meant respectively a mono- or divalent saturated aliphatic radical containing up to about eight carbon atoms, wherein the nitrogen of the alkylamino or alkylaminoalkylene may form a heterocycle with the alkyl or alkylene groups, wherein substituted phenyl may be substituted by, for example, alkyl, hydroxyl, alkoxy, halogen, nitro or amino, wherein heteroaryl may be, for example, 2-pyridyl.

These compounds are useful for observed pharmacological properties, particularly for action as anti-inflammatory agents. Compounds having such properties are known to be useful in the treatment of arthritis in warm-blooded animals.

PRIOR ART

The closest prior art known to applicant are Japanese Pat. No. 7,431,683 which discloses phthalazine derivatives, including certain phthalazinones, reported to be anti-inflammatory and anti-bacterial agents, having an alkoxy, oxo, or hydroxyl group at the fourth position and having no substituent for hydrogen in the sixth or seventh position and British Pat. No. 808,636 which fails to show any substitution in the aromatic ring of the phthalazinone nucleus.

SPECIFIC EMBODIMENTS OF THE INVENTION

The invention is more specifically illustrated by the following examples, which should be understood to be only representative of the invention and in no way a limitation on its scope. Some of the examples report results of tests which measured the anti-inflammatory ability of the compound produced. These properties were determined by carrageenan-induced paw edemas of test rats. Male, Sprague-Dawley rats (Blue Spruce Farm) were ordered at 124–140 g, housed for one week, and allowed food and water ad libitum. At the time of the experiments, only rats weighing 160–200 g were used.

All compounds were dissolved or suspended in a 0.5% water solution of Methocel and orally or intraperitoneally administered to groups of six rats each. Control rats received Methocel only. Two hours later (unless otherwise stated), paw edema was induced by subcutaneous injection into the plantar surface of the right hind paw of 0.1 ml of a 1.0% homogenized suspension of carrageenan.

Immediately, the volume of the paw was measured by immersing it in mercury to above the lateral mateolus. The mercury in a glass cylinder 22 mm in diameter and 60 mm deep was connected at the bottom of the cylinder by a column of water to a Statham transducer (model P23BB), range 0–5 cm of mercury pressure. The volume was recorded electronically on a Beckman recorder, R511. Three hours later, the inflamed paw volume was measured again, and the change in volume was recorded for each group. The percent inhibition of edema was calculated using the control group paw volume as 100% edema, i.e., $$\frac{\text{Control group edema } \Delta - \text{test group edema } \Delta}{\text{control group edema } \Delta} \times 100 =$$

% Inhibition of Edema

EXAMPLE 1

The steps followed in the procedure of this example are illustrated diagramatically below:

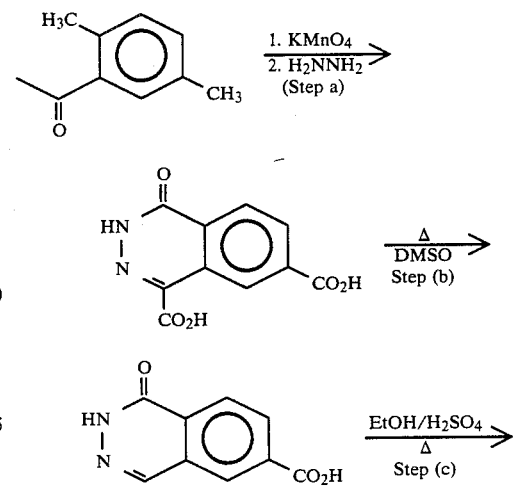

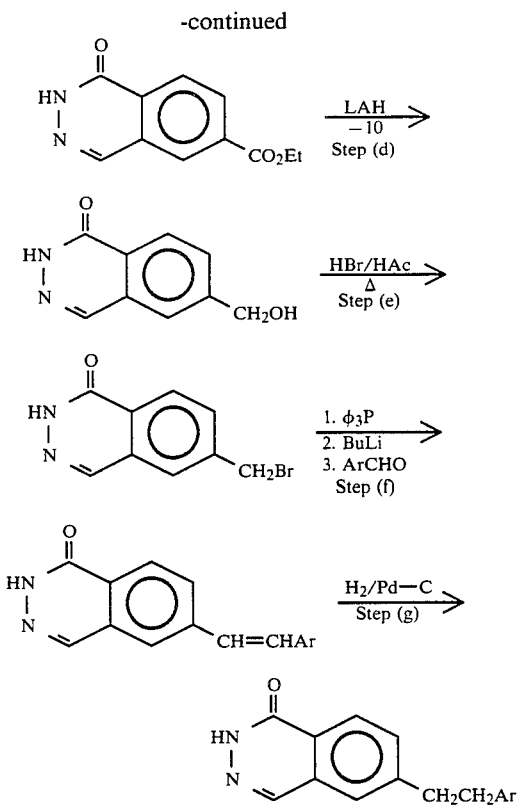

Step (a), Production of 1-(2H)-Oxophthalazine-4,6-dicarboxylic acid 2,5-Dimethylacetophenone (314 g) was added to 5000 ml water and treated with $K_2CO_3$ (266 g) and heated to 100°. Solid $KMnO_4$ (1965 g) was added portionwise over ca 2 hours, then the mixture was maintained at 100° for 1½ hours before allowing to cool. The $KMnO_4$ additions were rinsed in with about 500 ml $H_2O$.

The oxidation mixture was filtered and washed with 4×1000 ml water. The filtrate was heated to 90° and the pH was adjusted to 7. Hydrazine (138 ml) was added, and the mixture was allowed to stand overnight and then made strongly acid with 1000 ml conc HCL added all at once. It was stirred a few minutes and allowed to settle for about an hour. Clear supernatant was siphoned off and filtered and washed with 500+1000+3×1500 ml water. The product was air dried on a tray in a hood draft. Wt=294 g.

Step (b), Production of 1-(2H)-Oxophthalazine-6-carboxylic acid

The product from Step (a) (160 g) was added to 850 ml DMSO, and the mixture was refluxed for 2½ hours and allowed to cool. The product was filtered off, washed with a little DMSO, then with methanol and finally with diethyl ether. Dried in vacuo. Wt=62.5 g; m.p.>360°.

Step (c), Production of 1-(2H)-Oxophthalazine-6-carboxylic acid, ethyl ester The product from Step (b) (54 g) was added to 2000 ml ethanol, 10 ml conc $H_2SO_4$ was added, and the mixture was heated at 200° for 4 hours, cooled, filtered, washed and dried. Wt=37 g; m.p. 209°–211°.

Step (d), Production of 1-(2H)-Oxophthalazine-6 methanol

The product from Step (c) (23.1 g) was added portionwise to a solution of 6 g LAH in 500 ml THF, stirred for 1½ hours at about 0°, then the excess LAH was decomposed with 25 ml ethyl acetate. The reaction mixture was added to 750 ml ice and water, acidified with HCl and the THF stripped off on a rotovap. The product was filtered off and washed with water, isopropanol and diethyl ether. Wt=15.1 g; m.p. 230°–232°.

Step (e), Production of 6-Bromomethyl-1(2H)phthalazin-1(2H)-one 7.9 g of the product from Step (d) was refluxed in 75 ml HBr/HAc (30%) for 1 hour, cooled, diluted with 120 ml water, filtered, washed neutral with water, then washed with isopropanol and diethyl ether. Wt=8.9 g; m.p. 251°–260° dec.

Step (f), Production of 1-(2H)-Oxophthalazin-6-ylmethyltriphenylphosphonium bromide The product from Step (f) (8.6 g) and 10.5 g triphenyl phosphate were refluxed in DMF for 45 minutes, allowed to cool, filtered and washed with DMF and diethyl ether. Wt=14.6 g; m.p. 259°–260°.

Step (g), Production of Cis- and trans-6-[2-(4-methoxyphenyl)ethenyl]-1(2H)-phthalazinone Sodium hydride (0.95 g) in 20 ml DMSO was heated to 70°–75° for ca 45 minutes (until gas evolution ceased). The solution was then cooled in an ice bath, and a slurry of 19 g phosphonium salt from Step (f) in 60 ml DMSO was added over 5 minutes (temperature rose from 18° to 28°). The reaction mixture was stirred for 15 minutes, then 5.7 g p-anisaldehyde was added, and the reaction mixture was stirred for 60 minutes. The temperature rose from 20° to 38°, then slowly fell back.

Water (20 ml) was added to the reaction; then, after stirring for an hour, another 200 ml water was added and the product filtered off and washed with water. The damp cake was slurried in 200 ml isopropanol, filtered and washed with isopropanol and diethyl ether. Wt=8.0 g of material suitable for next step (an approximately 3:2 mixture of trans:cis isomers).

The isomer mixture can be recrystallized from DMF (7 ml/g) to give 3.5 g trans isomer melting at 290°–293°. A second recrystallization resulted in 3 g pure trans isomer melting at 292°–295°.

Removal of solvent from the filtrate from the first recrystallization followed by washing with ethanol yielded 3.9 g material melting at 204°–220° which was about 75% cis-product.

In one test wherein twelve rats (i.e. 6 control and 6 test animals) were subjected to the Carrageenan induced edema test described above using a dosage of 25 mg/kg of the compound of this example, a 43% inhibition of the tested over the control was observed.

Other species within the generic concept can be prepared following essentially the same procedure described above but substituting 4-chlorobenzaldehyde, 4-nitrobenzaldehyde, 4-methylbenzaldehyde for p-anisaldehyde to obtain:

6-[2-(4-chlorophenyl)ethenyl]-1(2H)-phthalazinone
6-[2-(4-nitrophenyl)ethenyl]-1(2H)-phthalazinone
6-[2-(4-methylphenyl)ethenyl]-1(2H)-phthalazinone

EXAMPLE 2

Trans-6-[2-(4-Hydroxyphenyl)ethenyl]-phthalazin-1(2H)-one

The product from Example 1 (24.3 g) was heated with 100 g anhydrous pyridine hydrochloride at 160° (bath temp. 180°) with stirring for about 4 hours, then poured while hot into 1000 ml water, stirred for 15 minutes, filtered, and washed with water, isopropanol and diethyl ether. Dry weight=19 g. Recrystallized from DMF (3 ml/g). Wt=14 g; m.p. 323°–324°. In one described Carrageenan induced edema test using a dosage of 25 mg/kg of the compound of this example, a 36.4% inhibition of the test compound over the control was observed.

EXAMPLE 3

Cis-6-[2-(4-Hydroxyphenyl)ethenyl]-1(2H)-phthalazinone

Trans-6-[2-(4-Hydroxyphenyl)ethenyl]-1(2H)-phthalazinone (12.4 gm) (produced in Example 2) was dissolved in 415 ml DMF by warming to 45° C. The solution was cooled back to 20° C. and diluted with an additional 200 ml DMF. The slightly cloudy solution was clarified by filtration, and the clear solution was irradiated in a soft glass container with 254 nm ultraviolet light for about 24 hours. The resulting solution was added with stirring to 6 L. water and allowed to settle for about 2 hours. The supernatant fluid, was decanted and the solid residue was filtered and washed with water and dried. Wt=7.4 gm, >95% cis by HPLC. mp=210°-22-° C (d).

EXAMPLE 4

6-(p-Hydroxyphenethyl)-1(2H)-phthalazinone

A solution of 2.2 gm 6-[2-[4-Hydroxyphenyl)ethenyl]-1(2H)phthalazinone (produced in Example 2) in 22 ml dimethylformamide was hydrogenated with 0.2 gm 10% palladium on charcoal at 50 psig for 3 hours. The catalyst was filtered off and the dimethylformamide removed in vacuo leaving 2 gm crude product melting at 216°–230°. Recrystallization from 40 ml isopropanol yielded 1 gm product melting at 235°–239°.

Other species within the generic concept can be prepared following essentially the same procedure described above but substituting 6-[2-(4-chlorophenyl)-ethenyl]-1(2H)phthalazinone, 6-[2-(4-nitrophenyl)ethenyl]-1(2H)-phthalazinone, 6-[2-(4-methylphenyl)ethenyl]-1(2H)-phthalazinone for 6-[2-(4-hydroxyphenyl)ethenyl]-1(2H)-phthalazinone to obtain:
6-(4-chlorophenethyl)-1(2H)-phthalazinone
6-(4-aminophenethyl)-1(2H)-phthalazinone
6-(4-methylphenethyl)-1(2H)-phthalazinone

EXAMPLE 5

6-(p-Methoxyphenethyl)-1(2H)-phthalazinone

The olefin from Example 1 (7.3 g) was slurried in 200 ml methanol and hydrogenated with 2 g 10% Pd-C at 60 psig for 2 hours. The product and catalyst was filtered off and the cake extracted twice with 75 ml boiling DMF, keeping extracts separate. The first extract, when cooled, yielded 5.1 g product; m.p. 206°–211°.

Removal of volatiles from all filtrates and mother liquors yielded 2 g crude product which yielded 1.2 g pure product when recrystallized from 10 ml DMF. In one described Carrageenan induced edema test using a dosage of 25 mg/kg of the compound of this example, a 14.5% inhibition of the test compound over the control was observed.

EXAMPLE 6

Cis- and trans-6-(2-phenylethenyl)-1(2H)-phthalazinone

A solution of dimsyl sodium in dimethylsulfoxide was prepared by heating 1.15 gm sodium hydride in 70 ml of dimethylsulfoxide at 70° until the gas evolution had ceased and a solution formed. The solution was cooled to 15° and a slurry of 21.1 gm 1(2H)-oxophthalazin-6-ylmethyl triphenyl phosphonium bromide (formed in Step (f) of Example 1) in 70 ml dimethylsulfoxide was added over about 10 minutes. The dark reddish brown solution was stirred for 15 minutes, then 5.3 gm benzaldehyde was added all at once. The temperature rose about 10° and the reddish tint disappeared from the brown solution.

After stirring for 3 hours the reaction was added to 1000 ml of water, stirred to a smooth slurry, filtered and washed with water. After air drying the product and the triphenylphosphine oxide were stirred to a smooth slurry in 125 ml isopropanol, filtered, washed with a little isopropanol, then slurried in 100 ml toluene, filtered, washed and dried. The crude product weighed 11.4 gm and melted at about 190°–200°. It could be recrystallized from n-butanol (7 ml/gm), but resulted in very little change in melting range. In one described Carrageenan induced edema test using a dosage of 50 mg/kg of the compound of this example, a 33.8% inhibition of the test compound over the control was observed.

EXAMPLE 7

6-Phenethyl-1(2H)-phthalazinone

A slurry of 11.2 gm 6-(2-phenylethenyl)-1(2H)-phthalazinone, from the previous example, in 115 ml dimethylformamide was hydrogenated with 1.0 gm 10% palladium on carbon catalyst at 50 psig for 3 hours. The catalyst was filtered off and rinsed with a little dimethylformamide. The filtrate was added to 5 volumes of water, stirred for a few minutes, filtered, washed with water and air dried. Wt=7.8 gm, m.p.=190°–193°. After recrystallization from 80 ml n-butanol the product weighed 6.4 gm and melted at 192°–193°.

EXAMPLE 8

The steps followed in the procedure of this example are illustrated diagrammatically below:

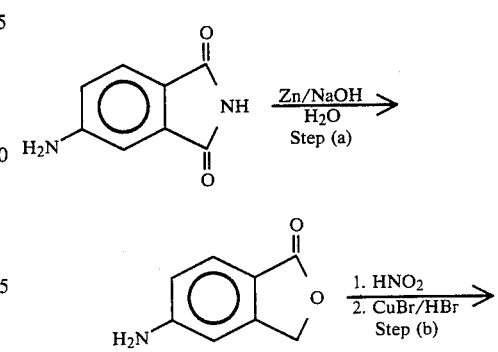

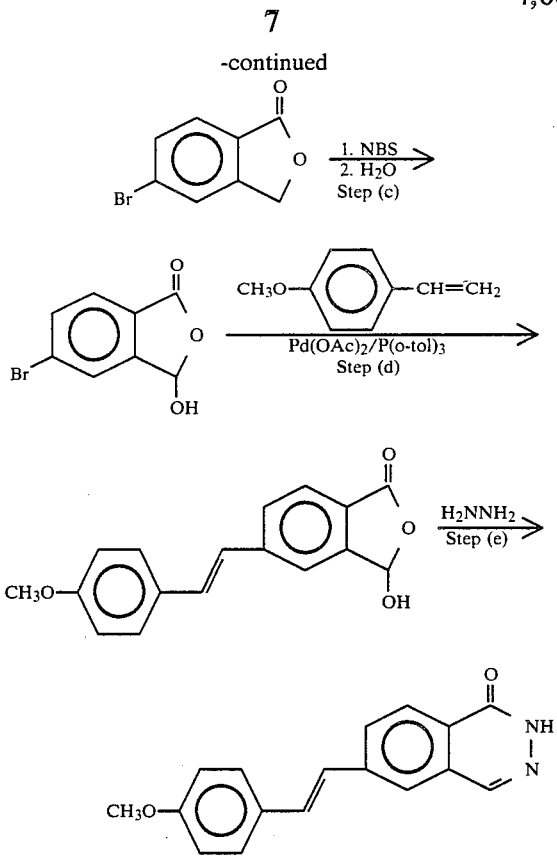

Step (a), Production of 5-Aminophthalide

Twenty grams of 4-aminophthalimide was added to a mixture of 41 gm zinc and 122 gm sodium hydroxide in 50 ml water (with good stirring) over 30 minutes. The mixture was stirred another 30 minutes, then heated to 60°. When ammonia ceased to be evolved the mixture was heated for an additional 60 minutes, then cooled to about 30°. The zinc residues were filtered off and the solution was acidified with 30 ml concentrated hydrochloric acid. The solution was heated to 90° for 45 minutes, then cooled and neutralized with 20 gm solid sodium carbonate, which brought the pH to 8–9. The product was filtered, washed with water and air dried. Wt=16.8 gm, m.p.=177°–189°.

Step (b), Production of 5-Bromophthalide

A mixture of 16.8 gm 5-aminophthalide in 34 ml 48% aqueous hydrobromic acid was cooled to 0° in an ice bath and a solution of 7.8 gm sodium nitrite in 15 ml water was added at less than 5°, using internal ice cooling as necessary. The nitrosation mixture was stirred for an additional 30 minutes at about 0° with an excess of nitrous acid (positive to starch-iodide test paper). After 30 minutes, the diazonium salt was added portion wise over about 35 minutes to a mixture of 28.2 gm freshly prepared cuprous bromide and 18 ml 48% aqueous hydrobromic acid at room temperature (the bulk of the diazonium salt was maintained at about 0°). The temperature of the reaction mixture rose to about 38° and considerable frothing occurred. The mixture was stirred for an hour, then the product was filtered off and washed neutral with water. After recrystallization from 100 ml isopropanol the product weighed 15.7 gm and melted at 153°–157°.

Step (c), Production of 5-Bromo-3-hydroxyphthalide

A mixture of 13.3 gm 5-bromophthalide and 12.7 gm N-bromosuccinimide in 480 ml carbon tetrachloride was irradiated with a tungsten floor lamp and refluxed for 3 hours. The reaction was followed by NMR. The succinimide was filtered off and the cake washed with carbon tetrachloride. The solvent was removed in vacuo leaving a residue of 19.2 gm, to which was added 100 ml water. This mixture was refluxed with stirring for 4 hours, then the mixture was cooled and the product filtered off, washed neutral with water and dried. Wt=9.9 gm.

Step (d), Production of Trans-5-[2-(4-methoxyphenyl)ethenyl]-3-hydroxyphthalide A mixture of 9.9 gm 3-hydroxy-5-bromophthalide, 5.8 gm p-methoxystyrene, 0.09 gm palladium acetate, 0.47 gm tri-(o-tolyl)-phosphine, 7 ml triethylamine and 35 ml dimethylsulfoxide were heated with stirring at 95° for 5 hours. The reaction mixture was cooled and added to 400 ml water. The product was extracted into ethyl acetate, which solution was washed with water and dried over magnesium sulfate. Removal of solvent left 8.0 gm yellow solid melting at 140°–148°.

Other species within the generic concept can be prepared following essentially the same procedure described above but substituting 4-chlorostyrene, 4-nitrostyrene, 4-acetoxystyrene for p-methoxystyrene to obtain:

Trans-5-[2-(4-chlorophenyl)ethenyl]-3-hydroxyphthalide
Trans-5-[2-(4-nitrophenyl)ethenyl]-3-hydroxyphthalide
Trans-5-[2-(4-acetoxyphenyl)ethenyl]-3-hydroxyphthalide.

Step (e), Production of Trans-6-[2-(4-methoxyphenyl)ethenyl]-1(2H)-phthalazinone Nine and one-half ml of hydrazine was added to a solution of 8.0 gm 5-(p-methoxyphenyl)ethenyl-3-hydroxyphthalide in 100 ml ethanol and the mixture was refluxed with stirring for 5 hours. The reaction mixture was cooled and the product filtered off and washed with isopropanol and dried. Wt=4.0 gm, m.p.=280°–289°.

Other species within the generic concept can be prepared following essentially the same procedure described above but substituting Trans-5-[2-(4-chlorophenyl)ethenyl]-3-hydroxyphthalide, trans-5-[2-(4-nitrophenyl)ethenyl]-3-hydroxyphthalide, trans-5-[2-(4-acetoxyphenyl)ethenyl]-3-hydroxyphthalide for 5-(p-methoxyphenyl)ethenyl-3-hydroxyphthalide to obtain:

Trans-6-[2-(4-chlorophenyl)ethenyl]-1(2H)-phthalazinone
Trans-6-[2-(4-nitrophenyl)ethenyl]-1(2H)-phthalazinone
Trans-6-[2-(4-acetoxyphenyl)ethenyl]-1(2H)-phthalazinone

EXAMPLE 9

The steps followed in the procedure of this example are illustrated diagramatically below:

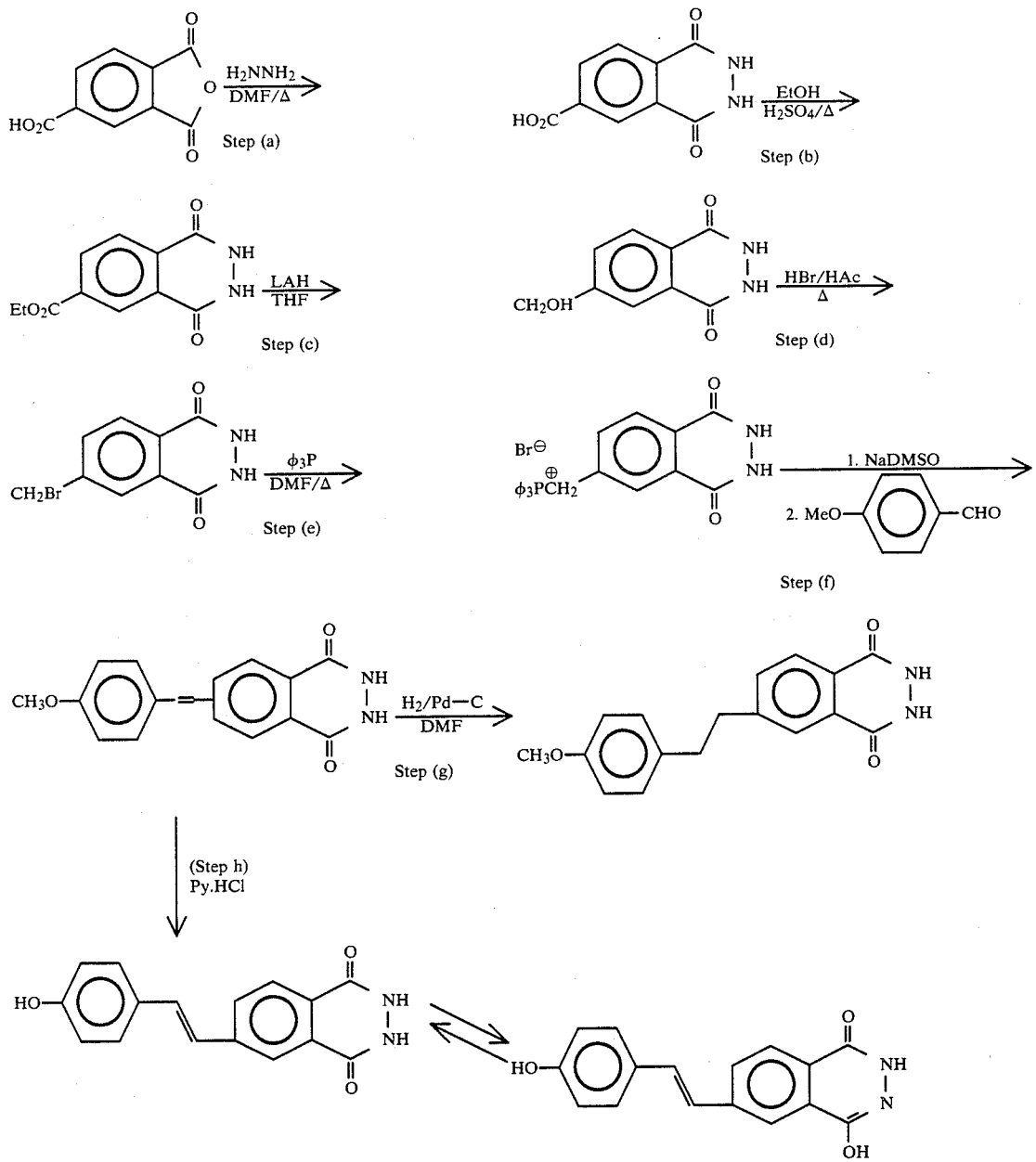

Step (a), Production of 1,4-Dioxo-2,3-dihydro-6-phthalazine carboxylic acid

A solution of 19.2 gm trimellitic anhydride in 200 ml dimethylformamide was heated to 100° and a solution of 9.6 gm hydrazine in 100 ml dimethylformamide was added over about one minute. A tar ball formed which eventually broke up on continued heating and stirring. The mixture was refluxed with stirring for any hour, cooled, filtered and washed with dimethylformamide and ether. Wt=19 gm.

Step (b), Production of 1,4-Dioxo-2,3-dihydro-6-phthalazinecarboxylic acid, ethyl ester The crude acid from the example above (32.5 g) was refluxed with stirring in 1600 ml absolute ethanol containing 50 ml concentrated sulfuric acid for 20 hours. The reaction mixture was cooled, filtered and washed with ethanol and dried. Wt=29.6 gm.

Step (c), Production of 1,4-Dioxo-2,3-dihydro-6-phthalazinemethanol

The solid ester from the example above (28.8 gm) was added to a solution of 8 gm lithium aluminum hydride in 500 ml tetrahydrofuran at 5° (ice bath cooling, very little heat evolution), then the temperature of the reaction was allowed to rise to room temperature. The mixture was stirred for 4 hours, then the excess lithium aluminum hydride was destroyed with 60 ml ethyl acetate, follow by 40 ml water, then 180 ml 6N hydrochloric acid. The mixture was diluted with another 500 ml water and the tetrahydrofuran was removed under vacuum. The product was then filtered off, washed with dilute hydrochloric acid and finally washed neutral with water before drying. Wt=22.2 gm, m.p.=280° dec.

Step (d), Production of 6-Bromomethyl-1,4-(2H,3H)-phthalazinedione

The alcohol from the previous example (22.7 gm) was added to 230 ml 30% hydrogen bromide in acetic acid. The mixture was stirred for ½ hour, then refluxed for 1½ hours. The reaction mixture was allowed to cool, which caused some of the product to crystallize out. The reaction mixture was diluted with 200 ml isopropanol, stirred for a few minutes, filtered and washed with isopropanol and then with water and dried. Wt=17.1 gm.

Step (e), Production of 1,4(2H,3H)dioxophthalazin-6-ylmethyl triphenylphosphonium bromide The bromo compound from the example above (17.2 gm) and 19 gm triphenylphosphine were refluxed in dimethylformamide for 1 hour. The reaction mixture was cooled, diluted with 700 ml toluene, stirred for a few minutes, filtered and washed with toluene and dried. Wt=34.2 gm.

Step (f), Production of Cis- and trans-6-[2-(4-methoxyphenyl)ethenyl]-1,4(2H,3H)-phthalazinedione A solution of dimsyl sodium in dimethylsulfoxide was prepared by heating 6.2 gm sodium hydride in 250 ml dimethyl sulfoxide at 70° for 60 minutes, then cooled the resulting solution down to about 12°. A solution of the phosphonium bromide from example 22 above (34 gm) in 150 ml dimethylsulfoxide was added at <20° and the mixture was stirred at about 15° for 15 minutes, then 30 ml p-anisaldehyde was added all at once, with ice bath cooling for the duration of the temperature rise in the reaction. The temperature rose to 30° during the first few minutes after the aldehyde addition, then started falling back. After stirring the reaction mixture for 4 hours, it was added to 3000 ml water, acidified with acetic acid, filtered and washed with water and sucked damp-dry. The crude cake was slurried in 500 ml acetone to remove triphenylphosphine oxide, filtered, washed with acetone and dried. (Isopropanol can be used in place of acetone, but it filters much more slowly.) Wt=13.3 gm. Recrystallization from DMF affords 8 g of the pure trans isomer, mp 345°-348° C. The cis isomer can be isolated from the filtrates on concentration.

Step (g), Production of 6-(p-methoxyphenethyl)-1,4-(2H,3H)-phthalazinedione

The olefinic compound from the example above (4 gm) in 80 ml dimethylforamide was hydrogenated at 50 psig with one gram 5% palladium on carbon for 1½ hours. The catalyst was filtered off, and the dimethylformamide solution concentrated to about 25 ml in vacuo. After allowing the product to partially crystallize out, the slurry was diluted with 75 ml. ether and stirred for several hours. The product was filtered off and washed with ether yielding 3.7 gm product melting at 247°-251°. The product had a light grey color. After recrystallization from 50 ml 2-methoxyethanol the product weighed 2.7 gm, melted at 250°-255°, and was light grey in color.

Step (h), Production of 6-(p-hydroxyphenethyl)-1,4-(2H,3H)-phthalazinedione

The corresponding hydroxy derivative can be made by treating the product of Step (G) with anhydrous pyridine hydrochloride employing the technique exemplified in Example 2.

In one Carrageenan induced edema test as described previously, using a dosage of 50 mg/kg of the methoxy derivative of this example, a 34% inhibition of the test compound over the control was observed.

EXAMPLE 10

The steps followed in the procedure of this example are illustrated diagrammatically below:

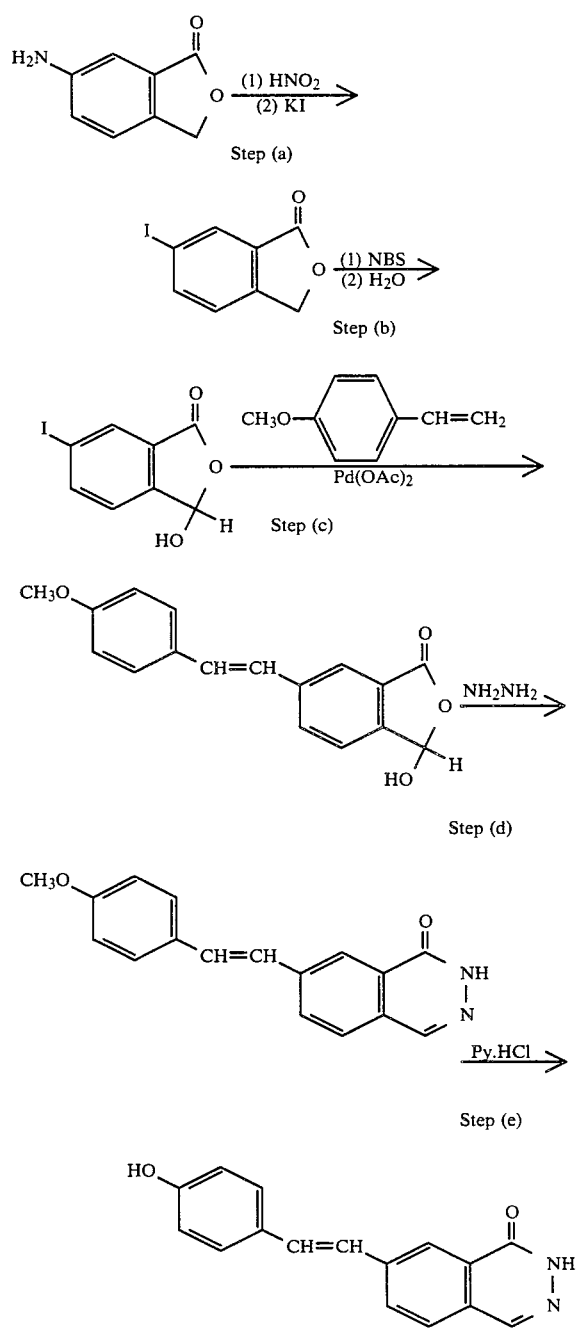

Step (a), Production of 6-Iodophthalide

The 6-iodophthalide was prepared in 23% yield via diazotization of 6-aminophthalide and subsequent treatment of the diazonium salt with potassium iodide according to the method of Tassman (*Rec. Trav. Chim. Pays-Bas,* 46, 653).

Step (b), Production of 6-Iodo-3-Hydroxyphthalide

To 2.5 g (9.6 mmol) of 6-iodophthalide suspended in 80 ml of CCl$_4$ was added 2.0 g (11.2 mmol) of NBS, followed by 10 mg of 2-azobisisobutyronitrile and the mixture was heated at reflux for 1 hour. The reaction mixture was then let cool to RT, finally in ice, and the solid (succinimide) was filtered off. The filtrate was evaporated to dryness affording the crude intermediary bromo-iodo phthalide as a pale yellow solid.

The above solid was suspended in 200 ml of H$_2$O and the mixture was heated at 100° for 2 hours—a clear solution was obtained after 20 minutes of heating. The solution was allowed to cool to RT, finally in ice, and the solid which formed was collected, washed well with cold H$_2$O, and dried in vacuo over P$_2$O$_5$; yield of colorless amorphous powder 2.29 g (86.3%).

Step (c), Production of 6-[2-(4-Methoxyphenyl)ethenyl]-3-hydroxyphthalide

A mixture of 1.38 g (5 mmol) of 6-iodo-3-hydroxyisobenzofuranone, 0.74 g (5.5 mmol) of p-methoxystyrene, 0.83 ml (5.5 mmol) Et$_3$N, 0.01 g of Pd (OAc)$_2$ and 1 ml of DMSO was prepared in a 10 ml flask. The flask was surmounted with a reflux condenser and the solution was heated to 95° (oil bath) with stirring under N$_2$ for 1 hour. The dark solution was allowed to cool to RT and poured onto 75 ml of ice/H$_2$O with stirring. After standing overnight, the solid which had formed was collected, washed well with cold H$_2$O and air dried. It was then heated with 50 ml of 95% EtOH, charcoaled and filtered. The reddish filtrate was cooled in ice and deposited 100 mg of reddish-brown solid which was found to be impurity and was discarded. The filtrate was evaporated at reduced pressure and the residual orange-yellow solid was triturated with 25 ml of Et$_2$O and filtered to afford 860 mg (60.9%) of the desired coupling product as a yellow solid; homogeneous by TLC—used as is for the next reaction.

Step (d), Production of Trans 7-[2-(4-Methoxyphenyl)ethenyl-1-(2H)-phthalazinone To 260 mg (0.92 mmol) 6-p-methoxystyryl-3-hydroxyphthalide dissolved in 25 ml of 95% EtOH was added 0.2 ml (4.1 mmol) of hydrazine and the yellow solution was heated at reflux for 1¼ hours. The solution was allowed to cool to RT, finally in ice, and the solid which had formed was collected, washed well with cold 95% EtOH and air dried; yield of pale yellow crystals 0.13 g (50.8%): m.p. 267°–269°.

Step (e), Production of trans-7-[2-(4-hydroxyphenyl)ethenyl]-1(2H)-phthalazinone Four grams of trans-7-[2-(4-methoxyphenyl)ethenyl]-1(2H)-phalazinone was sandwiched between 16 gm pyridine hydrochloride (divided into two approximately equal portions) and immersed in an oil bath that had been preheated to 180°. When the pyridine hydrochloride had melted, the mixture was stirred for 7 hours at 170°, then poured while still hot into 175 ml water with good stirring. Thirty milliliters of water was added to the residue in the flask. Both slurries were stirred until smooth, combined, filtered, washed with water and sucked damp-dry. The damp solid was slurried in 150 ml acetone, filtered, washed with acetone and dried. Wt=3.6 gm, m.p.=305°–308°.

The product was recrystallized from 35 ml 2-methoxyethanol plus 27 ml dimethylformamide. The recrystallization cake was washed with isopropanol and dried. Wt=2.5 gm, m.p.=308°–310°.

EXAMPLE 11

The steps followed in the procedure of this example are illustrated diagrammatically below:

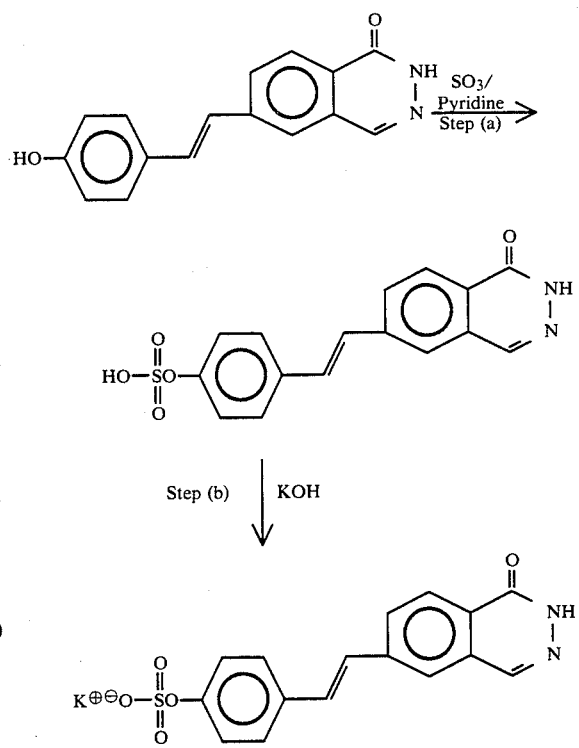

Steps (a) and (b), Production of potassium mono[trans-6-[2-(4-hydroxyphenyl)ethenyl]-1(2H)-phthalazinone]sulfate (a) A mixture of 20 g of trans-6-[2-(4-hydroxyphenyl)ethenyl]-1(2H)-phthalazinone (as prepared in Example 2), 950 ml of dry pyridine and 48.2 g of pyridine sulfur trioxide complex was heated at 60° C. for 1½ hours and then allowed to cool to room temperature. The solid was filtered and washed with ether. The crude pyridine salt of the sulfate ester weighed 45 g. (b) The pyridine salt was added to 300 ml of water containing 13 g of potassium hydroxide. A solution was obtained and then the potassium salt crystallized forming a thick suspension. The product was filtered, washed with a small amount of cold water, then with absolute ethanol and finally with some ether. Yield of the potassium salt of the sulfate ester was 22 g. The product was recrystallized twice from 200 ml of hot water; the solid was filtered and washed with absolute ethanol and then with ether. After drying in vacuum at room temperature, the product weighed 12.5 g.

EXAMPLE 12

Trans-6-[2-(4-Hydroxyphenyl)ethenyl]-2-(2,3dihydroxypropyl)-1(2H)-phthalazinone

To a solution of 26.5 gm trans-6-[2-(4-hydroxyphenyl)ethenyl]-1-(2H)-phthalazinone (as prepared in Example 2) in 300 ml DMSO was added 30 ml water, then 20 ml 45% KOH, then 31 gm 2,2-dimethyl-1,3-dioxolane-4-methanol p-toluenesulfonate ester. The mixture was stirred overnight, then added to 2000 ml ethylacetate, filtered and the residue washed with a little ethyl acetate. The solvent was removed from the filtrate on a rotary evaporator and the residue added to 1500 ml 25% aqueous sodium chloride. The product was extracted with three 500 ml portions of tetrahydrofuran, each extract being washed three times with saturated aqueous sodium chloride. The combined organic extracts were dried over magnesium sulfate, and the solvent removed on a rotary evaporator yielding 25.7 gm of a yellow solid. This was slurried in 40 ml chloroform, filtered and washed with chloroform leaving 5.5 gm crude product. Recrystallization from 30 ml n-butanol yielded 4.3 gm ketal melting at 193°–196° C.

The recrystallized ketal was refluxed in a mixture of 500 ml water, 50 ml methanol and 4.3 ml conc. hydrochloric acid for one hour. The mixture was cooled, filtered and washed with water, methanol and ether. The dihydroxypropyl derivative was dried. Weight=3.6 gm; mp 150°–153° C.

EXAMPLE 13

Trans-2-Butyl-6-[2-(4-hydroxyphenyl)ethenyl]-1(2H)-phthalazinone

A solution of 27.5 gm of trans-6-[2-(4-hydroxyphenyl)ethenyl]-1-(2H)-phthalazinone (as prepared in Example 2) in 1300 ml DMSO was treated with 135 ml 2.5N sodium hydroxide solution, followed by 12.5 ml n-butyl iodide. The reaction mixture was stirred for 2½ hours, then added to 8000 ml ethyl acetate. After stirring for a few minutes the insoluble material was filtered off and washed with a little ethyl acetate. The ethyl acetate was removed on a rotary evaporator and the residue added to 8000 ml water, stirred for an hour and allowed to settle overnight. The clear supernatant liquid was syphoned off and the residual slurry was filtered and the crude product washed thoroughly with water. After air drying it weighed 24.8 gm. The crude product was recrystallized from 125 ml 2-methoxyethanol, filtered and washed with isopropanol and ether. After drying at 60° for 24 hours, it weighed 17.4 gm and melted at 225°–230° C.

EXAMPLE 14

Trans-2-Heptyl-6-[2-(4-hydroxyphenyl)ethenyl]-1(2H)-phthalazinone

Using the same procedure and quantities as in Example 13 above, but substituting 17.5 ml n-heptyl iodide for the 12.5 ml n-butyl iodide used in the previous example, there was obtained, after recrystallization from 2-methoxyethanol, 21.1 gm product melting at 177°–178° C.

Other species within the generic concept can be prepared following essentially the same procedure described above but substituting methyl iodide, ethyl iodide, propyl bromide, amyl bromide, for butyl iodide to obtain:

Trans-2-methyl-6-[2-(4-hydroxyphenyl)ethenyl]-1(2H)-phthalazinone
Trans-2-ethyl-6-[2-(4-hydroxyphenyl)ethenyl]-1(2H)-phthalazinone
Trans-2-propyl-6-[2-(4-hydroxyphenyl)ethenyl]-1(2H)-phthalazinone
Trans-2-amyl-6-[2-(4-hydroxyphenyl)ethenyl]-1(2H)-phthalazinone

EXAMPLE 15

Trans-6-[2-(4-Hydroxyphenyl)ethenyl]-2-(3-dimethylaminopropyl)-1(2H)phthalazinone A solution of 19.8 gm trans-6-[2-(4-hydroxyphenyl)ethenyl]-1(2H)-phthalazinone (as prepared in Example 2) in 225 ml DMSO was treated sequentially with 25 ml water, 33 ml 45% aqueous KOH and 20 gm 3-dimethylaminopropyl chloride hydrochloride and the mixture was stirred at ambient temperature for eighteen hours. The reaction mixture was added to 2200 ml ethyl acetate and 300 ml water. The ethyl acetate was separated, washed twice with 300 ml water and dried over MgSO4. The solvent was removed on a rotovap.

Salt, 350 gm, was added to the aqueous layer, and the layer was extracted three times with 250 ml tetrahydrofuran, washing each extract 3 times with 75 ml of ¾ saturated salt solution. The THF solution was dried over MgSO4 and the solvent removed.

The residues from the solvent removal were treated with isopropanol (100 ml for THF residue, 70 ml for EtAc residue), filtered and washed with isopropanol and ether, Wgt from EtAc=2.7 gm; Wgt from THF=12.1 gm.

The crude free base was converted to the hydrochloride and recrystallized from 160 ml water plus 8 ml conc. HCl yielding 14.4 gm of product melting at 281°–283° C.

Other species within the generic concept can be prepared following essentially the same procedure described above but substituting 3-diethylaminopropyl chloride, 3-(1-piperidinyl)-propylchloride, 2-diethylaminoethyl chloride, 2-(1-pyrrol-idinyl)ethyl chloride for 3-dimethylaminopropyl chloride to obtain:
trans-6-[2-(4-hydroxyphenyl)ethenyl]-2-(3-diethylaminopropyl)-1(2H)-phthalazinone,
trans-6-[2-(4-hydroxyphenyl)ethenyl]-2-(3-(1-piperidinyl)propyl]-1(2H)-phthalazinone,
trans-6-[2-(4-hydroxyphenyl)ethenyl]-2-(2-diethylaminoethyl]-1(2H)-phthalazinone and
trans-6-[2-(4-hydroxyphenyl)ethenyl]-2-[2-(1-pyrrolidinyl)ethyl]-1(2H)-phthalazinone.

Others species within the generic concept can be prepared following essentially the same procedure described above but substituting trans-6-[2-(4-chlorophenyl)ethenyl]-1(2H)-phthalazinone, trans-6-[2-phenylethenyl]-1(2H)phthalazinone for trans-6-[2-(4-hydroxyphenyl)ethenyl]-1(2H)-phthalazinone to obtain:
trans-6-[2-(4-chlorophenyl)ethenyl]-2-(3-dimethylaminopropyl)-1(2H)-phthalazinone, and
trans-6-[2-phenylethenyl]-2-(3-dimethylaminopropyl)-1(2H)-phthalazinone

EXAMPLE 16

Trans-6-[2-(4-Hydroxyphenyl)ethenyl]-1(2H)-phthalazinone-2-propanoic acid

A solution of 19.8 gm trans-6-[2-(4-hydroxyphenyl)ethenyl]-1(2H)-phthalazinone in 225 ml DMSO was treated sequentially with 25 ml water, 23 ml 45% aqueous KOH and 13.6 gm ethyl 3-bromopropionate. The reaction mixture was stirred overnight, added to 1200 ml water, acidified with conc. HCl, filtered and the cake washed with water. The filter cake was stirred with 1300 ml water containing 15 gm $KHCO_3$ for about an hour, then 25 gm celite was added and the mixture filtered through a 24 cm Buchner funnel, washing the cake with water. The resulting clear solution was acidified and the product was filtered off, washed with water and dried. Wgt=11.7 gm mp=292°-295° C. After recrystallization from 50 ml DMSO plus 14 ml water, the product weighed 9.1 gm and melted at 294°-297° C.

EXAMPLE 17

Trans-2-(3-Dimethylaminopropyl)-6-[2-(4-methoxyphenyl)ethenyl]-1(2H)-phthalazinone A suspension of trans-5-(4-methoxyphenyl)ethenyl-3-hydroxyphthalide (85 gm) in isopropanol (450 ml) was treated with N-(3-dimethylaminopropyl)hydrazine (50 gm) and the mixture was refluxed for 1.5 hour. The precipitate was filtered from the cooled mixture and washed with cold isopropanol/ether to give the phthalazinone (74 g) mp 248°-250° C.

Other species within the generic concept can be prepared following essentially the same procedure described above but substituting trans-5-[2-(4-chlorophenyl)-ethenyl]-3-hydroxyphthalide, trans-5-[2-(4-nitrophenyl)-ethenyl]-3-hydroxyphthalide, trans-6-[2-(4-hydroxyphenyl)-ethenyl]-3-hydroxyphthalide for trans-5-]2-(4-methoxyphenyl)ethenyl]-3-hydroxyphthalide to obtain:

Trans-6-[2-(4-chlorophenyl)ethenyl]-2-(3-dimethylaminopropyl)-1(2H)phthalazinone Trans-6-(2-(4-nitrophenyl)ethenyl]-2-(3-dimethylaminopropyl)-1(2H)phthalazinone Trans-7-[2-(4-hydroxyphenyl)ethenyl]-2-(3-dimethylaminopropyl)-1(2H)phthalazinone

EXAMPLE 18

Trans-6-[2-(4-Methoxyphenyl)ethenyl]-2-(2-pyridyl)-1(2H)-phthalazinone

A suspension of trans-5-(4-methoxyphenyl)ethenyl-3-hydroxyphthalide (30 gm) in 175 ml of ethanol was heated until solution was effected. 2-Hydrazinopyridine (10.5 gm) was added portionwise; then the reaction was refluxed for 2 hours. The cooled reaction was filtered, and the precipitate was washed with ethanol and ether to give the phthalazinone which was recrystallized from dimethylformamide Wt=17.1 g, mp=213°-214° C.

EXAMPLE 19

Trans-6-[2-(4-Hydroxyphenyl)ethenyl]-2-(2-pyridyl)-1(2H)-phthalazinone

Trans-6-[2-(4-methoxyphenyl)ethenyl]-2-(2-pyridyl)-1(2H)-phthalazinone (7 g) and pyridine hydrochloride were thoroughtly mixed and heated to 180° C. for 2½ hours. The solution was cooled to about 120° C.; then DMF (30 ml) was added followed by water (80 ml). The mixture was cooled to 20° C., filtered and the precipitate was washed with isopropanol. The solid mass was recrystallized from DMF to give 3.7 g of the phenol, mp=272° C.

EXAMPLE 20

Cis-6-[2-(4-Dimethylaminophenyl)ethenyl]-1(2H)-phthalazinone 4-dimethylaminobenzaldehyde (9 gm) in DMSO (30 ml) was added to a solution of 1-oxo-2H-phthalazin-6-ylmethyl triphenylphosphonium bromide (0.04 mole) in DMSO (100 ml) and stirred overnight at room temperature. The reaction mixture was added to water (1 L), stirred, and the precipitate was filtered to give a solid. The solid was air dried, slurried with acetone (200 ml) and filtered and dried to give a mixture of cis and trans isomers (9.9 gm). The solid was recrystallized from DMF (65 ml) and filtered to give pure cis product (4.8 gm), mp=312°-318° C.

Concentration of the filtrates afforded a mixture of the cis and trans isomers as a solid.

EXAMPLE 21

6-[2-(4-Dimethylaminophenyl)ethyl]-1(2H)-phthalazinone

6-[2-(4-Dimethylaminophenyl)ethenyl]-1(2H)-phthalazinone (2.6 gm of a mixture of cis/trans isomers) in methanol (100 ml)/5N.HCl (10 ml) was hydrogenated at 60 psig over 5% Pd/C (0.5 gm) for 20 hours. The reaction mixture was heated to dissolve the product and then filtered from the catalyst. The cooled filtrate was filtered to give the saturated product as a solid (2.3 gm), mp 257°-9° C.

EXAMPLE 22

Trans-6-[2-(4-Methoxyphenyl)ethenyl]-2-phenyl-1(2H)-phthalazinone

Following the procedure of Example 18 above trans-5-[2-(4-methoxyphenyl)ethenyl]-3-hydroxyphthalide (15 g) and phenyl hydrazine (10 ml) were reacted to give the 2-phenyl-1(2H)-phthalazinone derivative (9.8 g), mp 198°-199° C.

Other species within the generic concept can be prepared following essentially the same procedure described above but substituting 2-chlorophenylhydrazine, 4-bromophenyl hydrazine, 4-nitrophenylhydrazine, 4-methylphenyl hydrazine for phenylhydrazine to obtain:

Trans-6-[2-(4-methoxyphenyl)ethenyl]-2-(2-chlorophenyl)-1(2H)-phthalazinone

Trans-6-[2-(4methoxyphenyl)ethenyl]-2-(4-bromophenyl)-1(2H)-phthalazinone

Trans-6-[2-(4-methoxyphenyl)ethenyl]-2-(4-nitrophenyl)-1(2H)-phthalazinone

Trans-6-[2-(4-methoxyphenyl)ethenyl]-2-(4-methoxyphenyl)-1(2H)-phthalazinone

EXAMPLE 23

Trans-6-[2-(4-Hydroxyphenyl)ethenyl]-2-(2-dimethylaminoethyl)-1(2H)-phthalazinone hydrochloride Following the procedure of Example 15 above trans-6-[2-(4-hydroxyphenyl)ethenyl]-1(2H)phthalazinone (19.8 ) and 2-dimethylaminoethyl chloride hydrochloride (17.3 g) were reacted to give the 2-(2-dimethylaminoethyl)derivative as the hydrochloride (16 g), mp 283°-285° C.

EXAMPLE 24

6-[2-(4-Hydroxyphenyl)ethyl]-2-(3-dimethylaminopropyl)-1(2H)-phthalazinone

Trans-6-[2-(4-Hydroxyphenyl)ethenyl]-2-(3-dimethylaminopropyl)-1(2H)-phthalazinone hydrochloride (5 g) in methanol (100 ml) and water (10 ml) was hydrogenated at 50 psi over 10% Pd/C (0.5 g). After 6 hours the catalyst was filtered and the filtrate was diluted with ether (600 ml). The precipitated product was filtered to give 4.3 g of the saturated product as the hydrochloride mp. 234°–236° C.

EXAMPLE 25

Trans-2-(3-Dimethylaminopropyl)-6-(2-phenylethenyl)-1(2H)-phthalazinone

Following the procedure of Example 8 above trans-3-hydroxy-5-(2-phenylethenyl)phthalide (63 g) was prepared from 5-bromo-3-hydroxyphthalide (58 g) and styrene (29 g), mp 139°–144° C. The phthalide (12.7 g) was then reacted with N-(3-dimethylaminopropyl)hydrazine (8.4 g) according to the method of Example 17 above to give the 2-substituted phthalazinone (13 g), mp 132°–133° C. The hydrochloride has an mp of 235°–237° C.

EXAMPLE 26

Trans-2-(2-Hydroxyethyl)-6-]2-phenylethenyl]-1(2H)-phthalazinone

Trans-3-Hydroxy-5(2-phenylethenyl)phthalide (12.7 g) in isopropanol (75 ml) was heated to reflux and 2-hydroxyethylhydrazine (6 g) was added. After refluxing for 2 hours the reaction was cooled to 0° C. and the precipitate was filtered and washed with isopropanol to give the 2-(2-hydroxyethyl)derivative (11 g), mp 154°–156° C.

EXAMPLE 27

Trans-6-[2-(4-Hydroxyphenyl)ethenyl]-2-methyl-1(2H)-phthalazinone

Trans-3-Hydroxy-5-[2-(4-methoxyphenyl)ethenyl]phthalide (15 g) was dissolved in refluxing ethanol (85 ml) and methylhydrazine (10 ml) was added slowly. The resulting suspension was refluxed for 3 hours, then cooled and filtered to give the 2-methyl-1(2H)-phthalazinone, mp 223°–225° C. The methoxy phthalazinone (10 g) was mixed with pyridine hydrochloride (35 g) and heated to 180° C. for 10 hours. The mixture was diluted with water, filtered and washed with isopropanol to give the desired phenol (4.3 g), mp 282°–284° C.

EXAMPLE 28

Trans-6-[2-(4-Carboxyphenyl)ethenyl]-1(2H)-phthalazinone (a)
Trans-5-[2-4-Carboxyphenyl)ethenyl]-3-hydroxyphthalide 5-Bromo-3-hydroxyphthalide (48.3 g) was dissolved in DMSO (55 ml) and acetone (55 ml). 4-Carboxystyrene (35 g) triethylamine (66 ml), tri-o-tolylphosphine (0.6 g) and palladium acetate (0.31 g) were added to the solution and the mixture was refluxed for 18 hours. The cooled reaction was diluted with water (2 l) and basified with 2.5N.NaOH. The solvents were removed on the rotary evaporator and the remaining solution was filtered, acidified with 2.5N.HCl and filtered from the precipitated crude phthalide.

(b)
Trans-6-[2-(4Carboxyphenyl)ethenyl]-1(2H)-phthalazinone

The crude phthalide (69.4 g) was dissolved in ethanol (500 ml) and thereafter hydrazine (75 ml) was added. The reaction mixture was heated to 60° C. for 2 hours. The cooled mixture was filtered to give the phthalazinone as a solid (58.6 g), mp >345° C.

EXAMPLE 29

Trans-6-[2-[4-[3-Dimethylaminopropyl]aminocarbonylphenyl]ethenyl]-1(2H)-phthalazinone Trans-6-(2-(4-Carboxyphenyl)ethenyl]-1(2H)-phthalazinone (46 g), thionyl chloride (315 ml) and DMF (2 ml) were mixed and heated slowly to 42° C. and maintained at 42°–48° C. until the gas evolution subsided. The reaction mixture was diluted with toluene and filtered to give the crude acid chloride (52 g). The crude acid chloride (25 g) was dissolved in THF (1250 ml) and 3-dimethylaminopropylamide (250 ml) was added dropwise. After stirring overnight at room temperature the precipitate was filtered, washed with ether (2 l) and then dried to give the amide (13.5 g). The amide was purified via the hydrochloride salt, mp 287° C.

EXAMPLE 30

Trans-6-[2-[4-[3-Dimethylaminopropoxy]carbonylphenyl]ethenyl]-1(2H)-phthalazinone The acid chloride (25 g) of Example 29 above was dissolved in THF (1250 ml) and 3-dimethylaminopropanol (250 ml) was added dropwise. After stirring overnight at room temperature ether (2 l) was added and the resulting precipitate was filtered. The crude ester (13.6 g) was purified via the hydrochloride salt, mp 288° C.

EXAMPLE 31

Trans-6-[2-Phenylethenyl]-1-(2H)-phthaazinone

Following the procedure of Example 8 step e 3-hydroxy-5-(2-phenylethenyl)phthalide (5.7 g) and hydrazine (6 g) were reacted in ethanol (50 ml) to give the desired trans 6-[2-ophenylethenyl]-1(2H)-phthalazinone (2.8 g), mp 243°–244° C.

It will be apparent, however to those skilled in this art from a reading of the above that many modifications and changes may be made without departing from the scope and spirit of the invention.

What is claimed is:

1. A phthalazin-1(2H)one of the formula

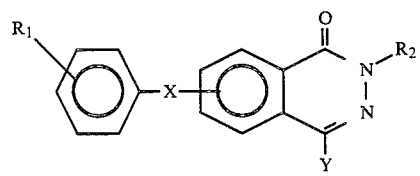

wherein
X is ethenylene and is substituted for hydrogen in the sixth or seventh position of the 1(2H)-phthalazinone ring, Y is a member of the class of hydrogen and hydroxyl,
$R_1$ is a member of the class of hydrogen, alkyl, $C_1$–$C_8$ alkoxy, hydroxyl, halogen, nitro, —$NR_3R_4$, the heterocycle

—$COR_5$ and —$OSO_3H$ or an alkali metal salt thereof,
$R_2$ is a member of the class of hydrogen, alkyl, phenyl, substituted phenyl, pyridyl, hydroxyalkyl, polyhydroxyalkyl, aminoalkyl, monoalkylaminoalkyl, dialkylaminoalkyl, carboxyalkyl, and the heterocycle-containing groups

and

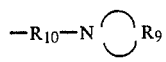

$R_3$, $R_4$ are independently from the class of hydrogen, alkyl, aminoalkyl, monoalkylaminoalkyl, dialkylaminoalkyl and the heterocycle containing groups

and

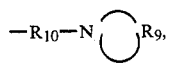

$R_5$ is a member of the class of $OR_3$,

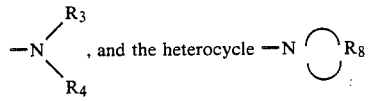

$R_6$ is a trivalent alkylene, $R_7$ is alkyl,
$R_8$ is alkylene,
$R_9$ is alkylene,
$R_{10}$ is alkylene
and wherein by alkyl and alkylene is meant respectively a mono- or divalent saturated aliphatic radical containing up to about eight carbon atoms, wherein substituted phenyl may be substituted by alkyl, hydroxyl, alkoxy, halogen, nitro, or amino.

2. The compound of claim 1 wherein X is ethenylene and Y is hydrogen.
3. The compound of claim 2 wherein $R_1$ is 4-methoxy, $R_2$ is hydrogen and X is substituted on the 6 position of the phthalazinone ring.
4. The cis form of the compound of claim 3.
5. The trans form of the compound of claim 3.
6. The compound of claim 2 wherein $R_1$ is hydroxyl, $R_2$ is hydrogen and X is substituted on the 6 position of the phalazinone ring.
7. The cis form of the compound of claim 6.
8. The trans form of the compound of claim 6.
9. The compound of claim 2 wherein $R_1$ and $R_2$ are hydrogen and X is substituted on the 6 position of the phalazinone ring.
10. The cis form of the compound of claim 9.
11. The trans form of the compound of claim 9.
12. The compound of claim 2 wherein X is substituted on the 7 position of the phthalazinone ring.
13. The compound of claim 12 wherein $R_1$ is hydroxy and $R_2$ is hydrogen.
14. The trans form of the compound of claim 13.
15. The compound of claim 2 wherein $R_1$ is methoxy and $R_2$ is dimethylaminopropyl.
16. The compound of claim 15 in the trans form.
17. The compound of claim 16 that is trans-2-(3-dimethylaminopropyl)-6-[2-(4-methoxyphenyl)-ethenyl]-1(2H)-phthalazinone.
18. A compound of claim 1 wherein $R_1$ is methoxy.
19. The compound of claim 2 wherein X is substituted on the 6 position of the phthalazinone ring and $R_1$ is $OSO_2^-K^+$.
20. The compound of claim 2 wherein X is substituted on the 6 position of the phthalazinone ring and $R_1$ and $R_2$ are hydrogen.
21. The compound of claim 2 wherein X is substituted on the 6 position of the phthalazinone ring and $R_1$ is methoxy and $R_2$ is hydrogen.
22. The compound of claim 2 wherein $R_1$ is hydroxyl and $R_2$ is dimethylaminopropyl.
23. The compound of claim 2 wherein $R_1$ is hydroxyl and $R_2$ is dimethylaminoethyl.

* * * * *